(12) United States Patent
Badalamenti et al.

(10) Patent No.: US 6,361,552 B1
(45) Date of Patent: Mar. 26, 2002

(54) TEETHING GEL APPLICATOR WITH CUTTER, AND BURSTABLE AMPULE AND METHOD OF MAKING THE SAME

(75) Inventors: Michael J. Badalamenti, 1218 Surfside Cir., Aurora, OH (US) 44202; Mark A. Sedlack, Cuyahoga Falls, OH (US)

(73) Assignee: Michael J. Badalamenti, Aurora, OH (US)

( * ) Notice: Subject to any disclaimer, the term of this patent is extended or adjusted under 35 U.S.C. 154(b) by 0 days.

(21) Appl. No.: 09/406,218

(22) Filed: Sep. 27, 1999

Related U.S. Application Data

(63) Continuation-in-part of application No. 09/047,714, filed on Mar. 25, 1998, now Pat. No. 5,957,954.

(51) Int. Cl.$^7$ ................................................ A61J 17/00
(52) U.S. Cl. ...................................................... 606/235
(58) Field of Search ........................ 606/235; 424/433, 424/436, 453; 604/218, 58–64, 411, 414, 415; 206/528, 532, 530, 539, 219, 222, 538, 469; 53/471; 222/541

(56) References Cited

U.S. PATENT DOCUMENTS

| | | | |
|---|---|---|---|
| 1,510,260 A | 9/1924 | Cyrenius | |
| 1,897,723 A | * 2/1933 | Free | 206/538 |
| 2,102,885 A | * 12/1937 | Carroll | 206/222 |
| D136,206 S | 8/1943 | Allen | |
| 2,705,011 A | 3/1955 | Newton | |
| 3,228,789 A | 1/1966 | Glassman | |
| 3,613,955 A | * 10/1971 | Wetherell, Jr. | 206/222 |
| 3,650,084 A | * 3/1972 | Moreland | 53/471 |
| 3,669,117 A | 6/1972 | Herbst | 606/235 |
| 3,732,865 A | * 5/1973 | Higuchi et al. | 424/453 |
| 4,439,197 A | 3/1984 | Honda et al. | |
| 5,013,321 A | 5/1991 | MacVane | |
| 5,037,623 A | * 8/1991 | Schneider et al. | 206/222 |
| 5,122,056 A | 6/1992 | Barbee | |
| 5,196,002 A | 3/1993 | Hanover et al. | |
| 5,211,559 A | 5/1993 | Hart et al. | |
| 5,277,912 A | 1/1994 | Lowe et al. | |
| 5,318,824 A | * 6/1994 | Itaya et al. | 206/538 |
| 5,403,349 A | 4/1995 | Rohrig | 606/234 |
| 5,810,886 A | 9/1998 | Hassan | 606/234 |

* cited by examiner

Primary Examiner—Henry J. Recla
Assistant Examiner—(Jackie) Tan-Uyen T. Ho
(74) Attorney, Agent, or Firm—Pearne & Gordon LLP

(57) ABSTRACT

A teething gel system and a burstable ampule for use therewith. The teething gel system includes a teether with a chewing portion defining a plurality of depressions for holding gel. A gel spreader is provided for movement across the teether so that gel is deposited into the depressions. The gel spreader includes a housing sized to receive the ampule. A cutter is disposed in the housing and is adapted to burst the ampule when the ampule is inserted into the housing. The ampule includes an inner sleeve formed of rigid material and an outer sleeve formed of frangible material.

22 Claims, 4 Drawing Sheets

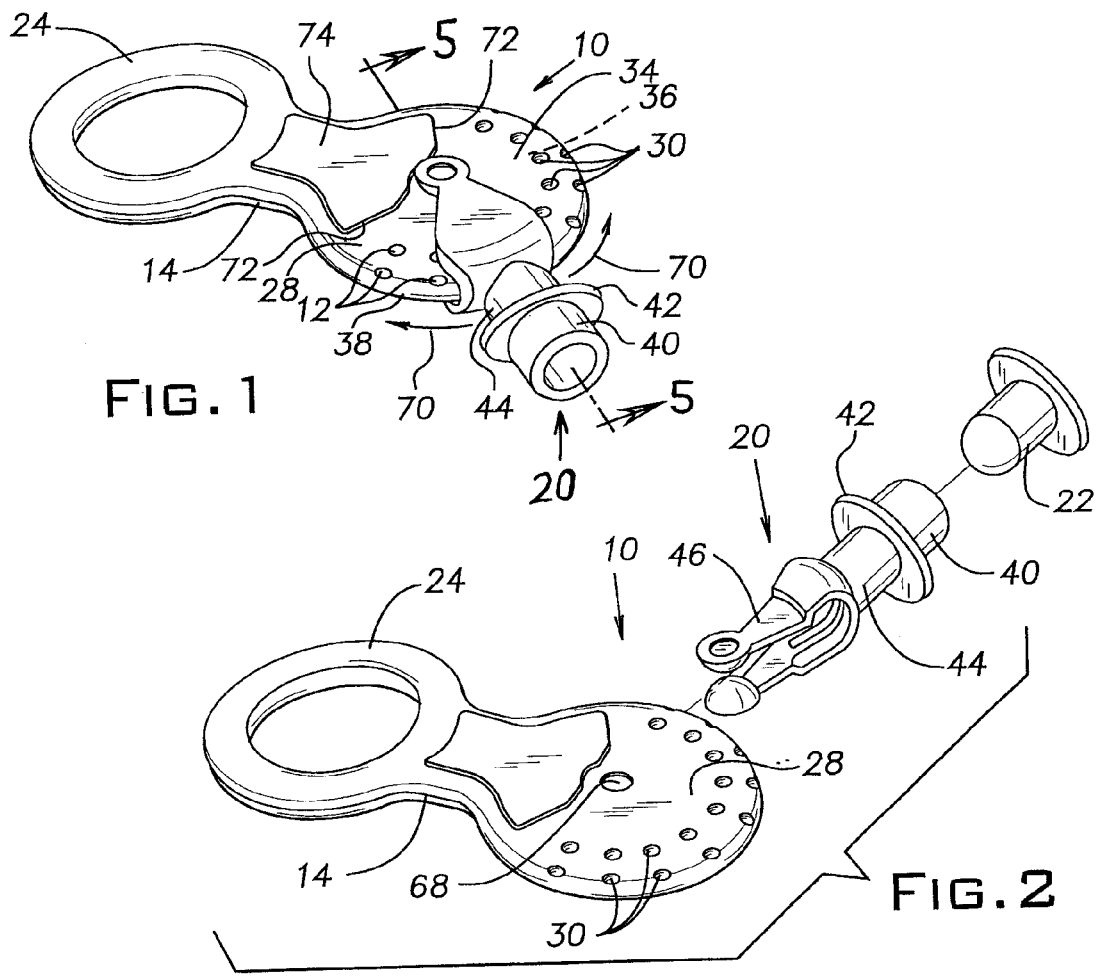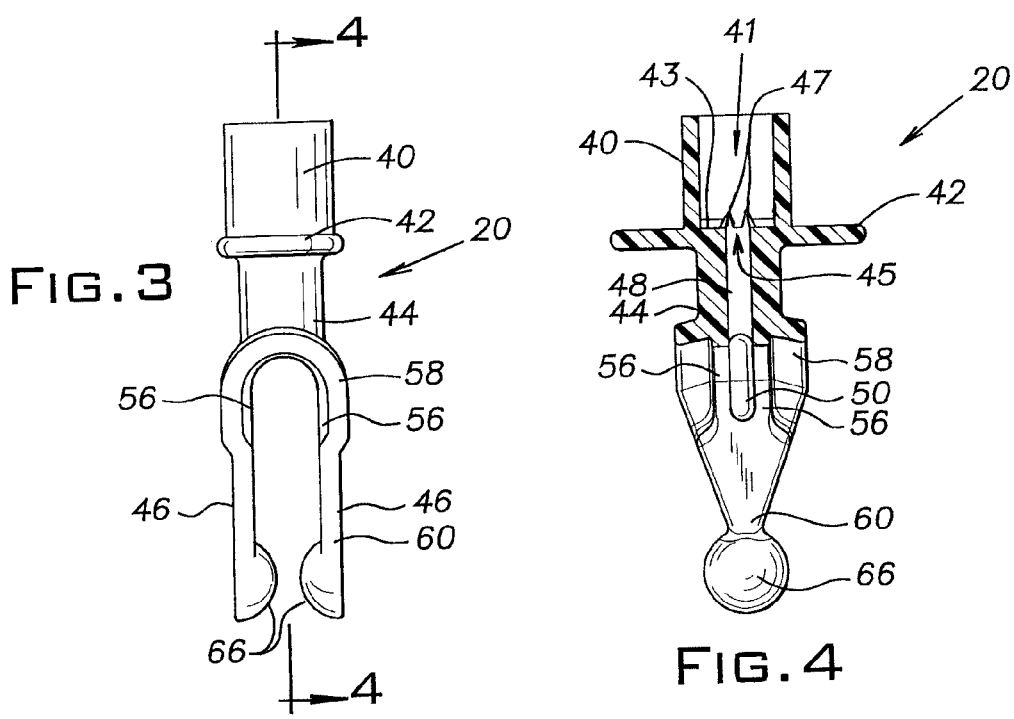

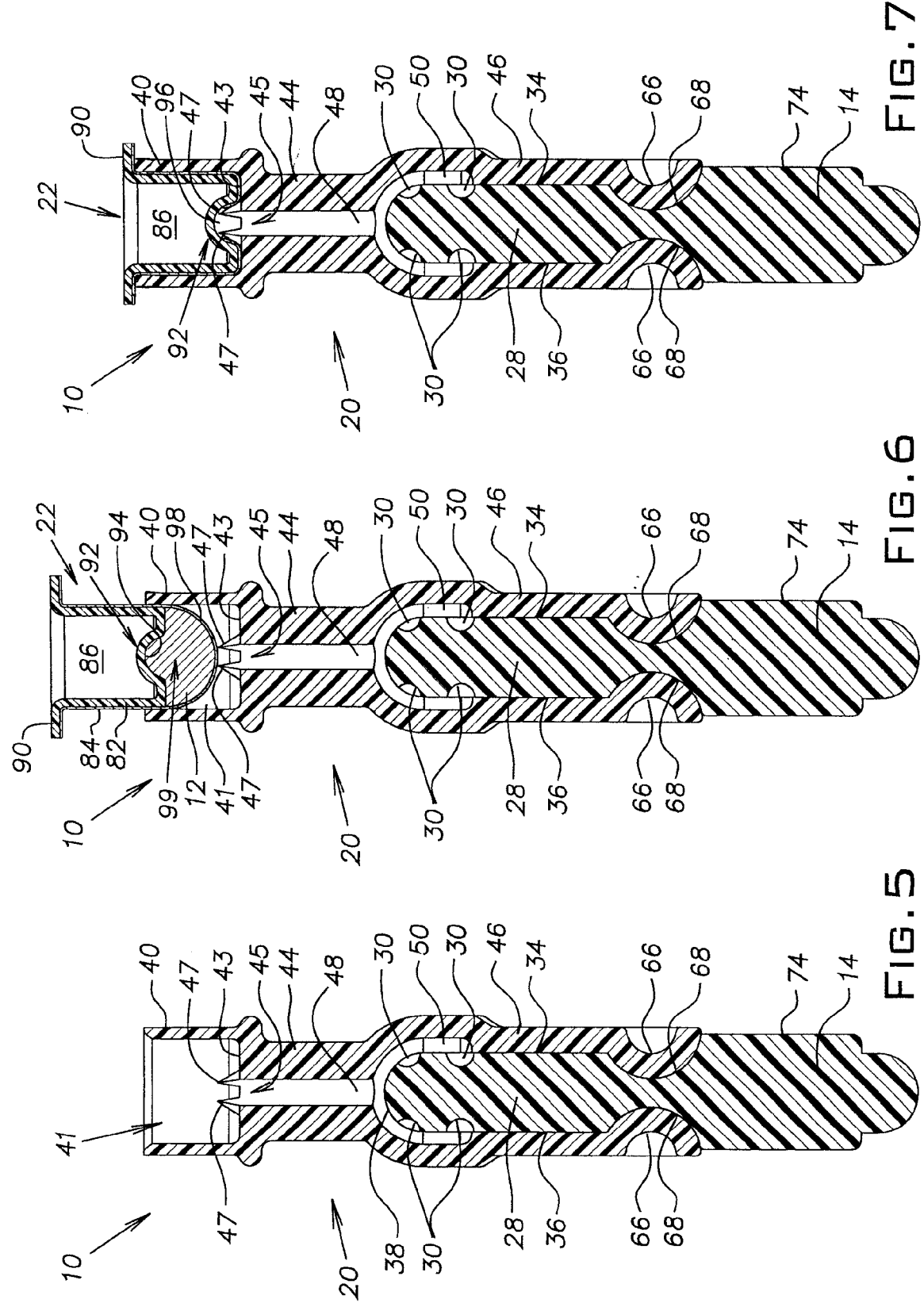

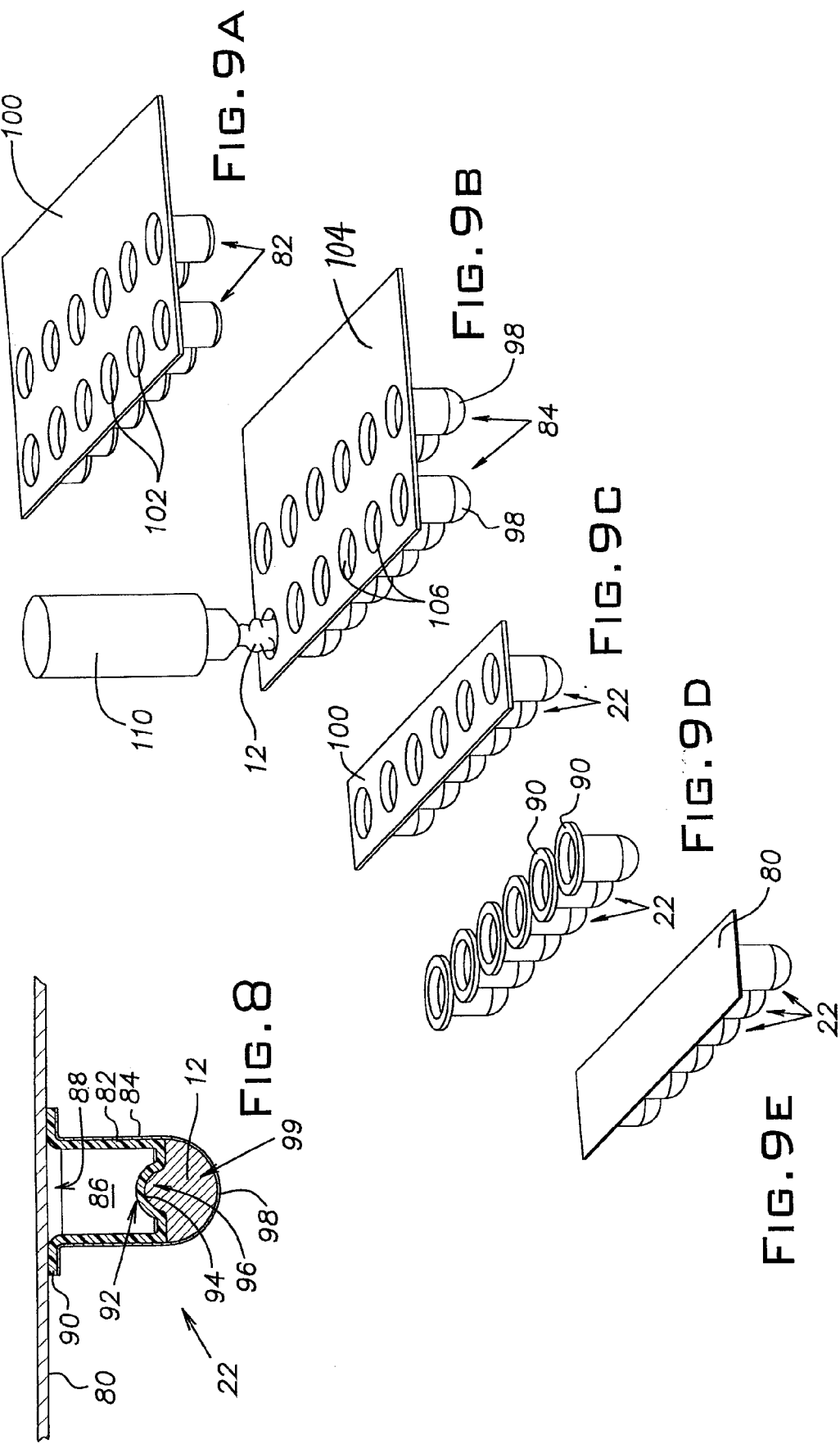

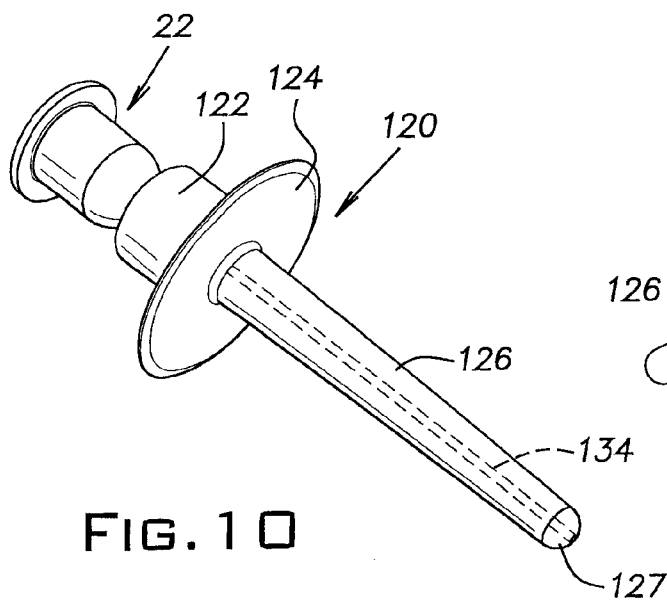
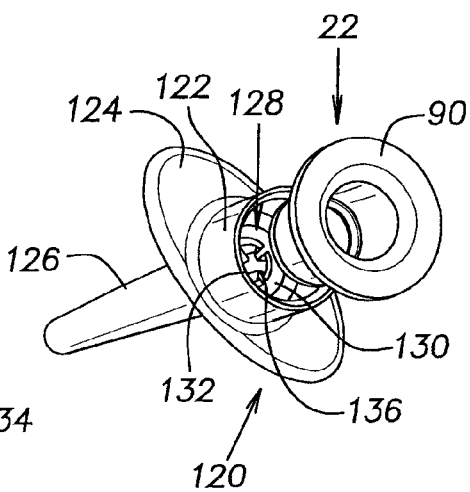
FIG. 10
FIG. 11
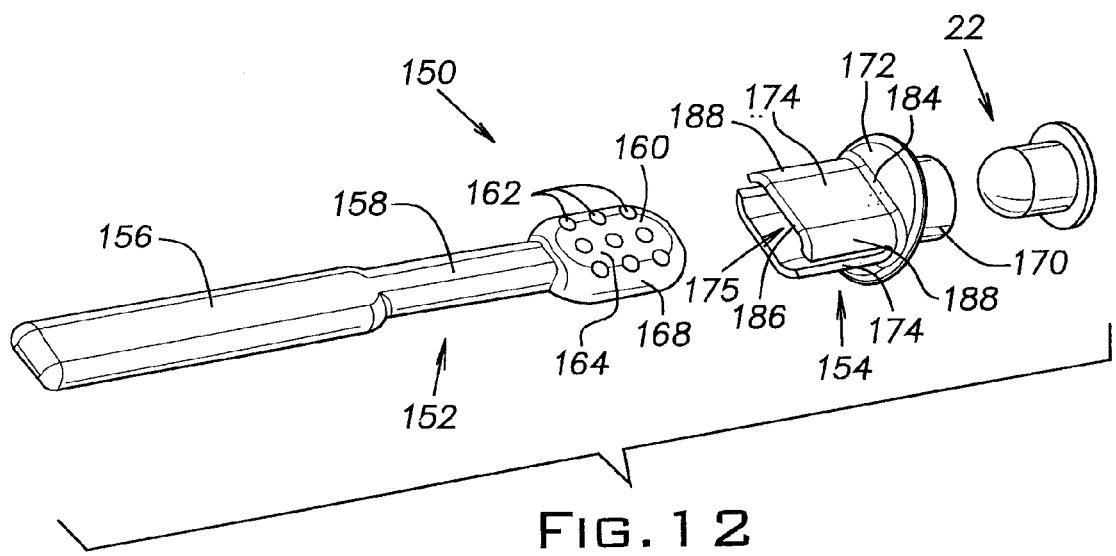
FIG. 12
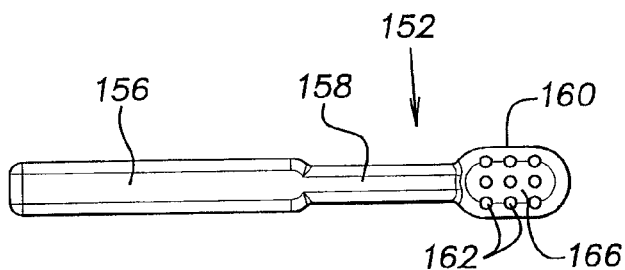
FIG. 13
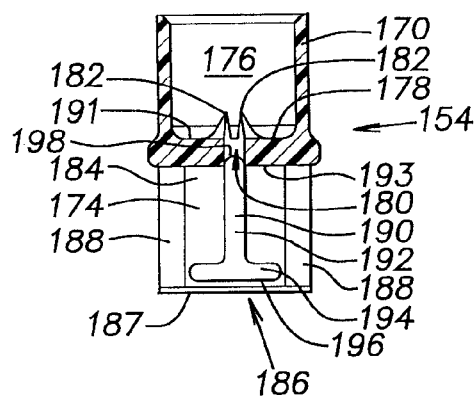
FIG. 14

TEETHING GEL APPLICATOR WITH CUTTER, AND BURSTABLE AMPULE AND METHOD OF MAKING THE SAME

CROSS-REFERENCE TO RELATED APPLICATIONS

This application is a continuation-in-part of application Ser. No. 09/047,714, filed Mar. 25, 1998, U.S. Pat. No. 5,957,954.

BACKGROUND OF THE INVENTION

The present invention generally relates to medication packaging and applicators. More specifically, the present invention relates to a medication applicator and a medication ampule for use therewith, wherein the medication applicator may be used to apply soothing gel to the gums of a child or an adult.

Both children and adults experience periodontal pain. Adults may experience periodontal pain as a result of gum disease, infection, or irritation from foreign objects, such as dentures. Infants and small children experience periodontal pain as a result of teething.

Teething is the physiological process of tooth eruption through the gums of the mouth, and typically begins between the ages of four and eight months. Once teething commences, it continues until all twenty childhood teeth are in place at approximately thirty months. Some of the manifestations resulting from the discomfort of teething include drooling, irritability, sleeping problems and biting on hard objects. The discomfort is caused by the pressure that erupting teeth place on the periodontal membrane. Pain can occur before visually perceptible eruption takes place.

There are presently several remedies for alleviating periodontal pain. These remedies include having the child or adult suck on a cool object. However, this quickly looses effectiveness as the object warms. Other remedies include pain relievers such as acetaminophen and ibuprofen. Also available are homeopathic medications, typically in the form of teething tablets. These remedies have significant drawbacks. Acetaminophen and ibuprofen are not recommended for children under two years old unless directed by a physician. Relief is also delayed until the drug travels through the bloodstream and takes effect. Another remedy is applying a topical anesthetic, such as benzocaine, to the affected area. However, topical products are difficult to apply in the correct dosage to the affected areas since they are currently applied with a fingertip, a cotton applicator or a syringe. In addition, with regard to children, the administrator must guess where the pain is emanating from, especially before visually perceptible eruption occurs.

SUMMARY OF THE INVENTION

The present invention overcomes these disadvantages by providing a teething gel system including a gel applicator. The gel applicator is for use with a burstable ampule containing a gel, and includes a housing having an interior wall at least partially defining an interior chamber. The interior chamber is adapted to receive at least a portion of the ampule. A cutter extends from the interior wall and is adapted to burst the ampule when the ampule is pushed into the interior chamber. A guide is provided for directing the gel to a desired location. The guide is connected to the housing and at least partially defines a channel that is in communication with the interior chamber.

Also provided in accordance with the present invention is a burstable ampule for holding an amount of medication. The burstable ampule includes an inner sleeve with a closed end. The inner sleeve is composed of a rigid material. An outer sleeve is disposed over the inner sleeve and has an end wall spaced from the closed end of the inner sleeve so as to form a pocket therebetween. The outer sleeve is composed of a frangible material. The pocket contains the medication.

BRIEF DESCRIPTION OF THE DRAWINGS

These and further features of the present invention will be apparent with reference to the following description and drawings, wherein:

FIG. 1 is a perspective view of a teething gel system according to a first embodiment of the present invention;

FIG. 2 is an exploded perspective view of the teething gel system of the first embodiment;

FIG. 3 is an elevational view of a gel applicator in the teething gel system of the first embodiment;

FIG. 4 is a cross sectional view of the gel applicator taken along line 4—4 of FIG. 3;

FIG. 5 is a cross sectional view of the teething gel system taken along the line 5—5 in FIG. 1;

FIG. 6 is a cross sectional view of the teething gel system of the first embodiment with an ampule partially disposed in a housing of the gel applicator;

FIG. 7 is a cross sectional view of the teething gel system of the first embodiment with the ampule fully disposed in the housing of the gel applicator;

FIG. 8 is a cross sectional view of the ampule;

FIGS. 9A–9E show steps in a method of forming a plurality of ampules;

FIG. 10 shows a side perspective view of a gel applicator according to a second embodiment of the present invention;

FIG. 11 shows a rear perspective view of the gel applicator according to the second embodiment of the present invention;

FIG. 12 shows a side perspective view of a teething gel system according to a third embodiment of the present invention;

FIG. 13 shows a bottom view of a teether of the teething gel system according to the third embodiment; and FIG. 14 shows a cross sectional view of a gel applicator of the teething gel system according to the third embodiment.

DETAILED DESCRIPTION OF THE PREFERRED EMBODIMENTS OF THE INVENTION

In the detailed description which follows, identical components have been given the same reference numerals, and, in order to clearly and concisely illustrate the present invention, certain features may be shown in somewhat schematic form. When a preferred range, such as 5 to 25 is given, this means preferably at least 5 and preferably not more than 25.

Referring to FIGS. 1 and 2, a first embodiment of the present invention is shown. More specifically, FIGS. 1 and 2 show a teething gel system 10 used to dispense an exact amount of medication 12 to a teething child's erupted or pre-erupted gum area. The teething gel system 10 is adapted for use with a burstable ampule 22 containing medication 12, and generally includes a teether 14, and a gel spreader or gel applicator 20. The teether 14 has a handle 24 and a chewing portion 28 provided with depressions or dimples 30 to hold the medication 12.

The teething gel system 10 takes advantage of the fact that a teething child will naturally take an object and direct it to an affected area in his or her mouth. Accordingly, the child can help in applying medication to a painful place in his or her mouth by chewing on the medicated chewing portion 28 of the teether 14. The handle 24 is provided to assist the child in holding the teether 14 and directing the chewing portion 28 to the correct location. Thus, the handle 24 has a shape that is easily grasped and held by an infant or toddler. For example, the handle 24 may be cylindrically shaped, or ring or toroidal shaped as shown in FIGS. 1 and 2.

The chewing portion 28 is preferably circular in shape and has a top surface 34, a bottom surface 36 (shown in FIGS. 5–7) and an edge 38. The edge 38 is rounded over to form a continuously smooth surface extending from the top surface 34 to the bottom surface 36. As mentioned, the chewing portion 28 is provided with a series of dimples 30. Each dimple 30 is preferably hemispherically shaped and about 1.5 to 6 mm in diameter, more preferably 2 to 3 mm in diameter, and about 0.5 to 3 mm in depth, more preferably 1 to 1.5 mm in depth. The dimples are arranged on both the top surface 34 and the bottom surface 36, and are located adjacent the rounded edge 38. Some of the dimples 30 are preferably located on the curved surfaces between the top surface 34 and the edge 38, and the bottom surface 36 and the edge 38 respectively (best seen in FIGS. 5–7).

The dimples 30 hold the medication 12 by surface tension. The preferred medication 12 for use with the teething gel system 10 is a gel preparation containing 7% benzocaine to act as a topical anesthetic. Other known anesthetic gels may be used. The dosage is determined by the volume of the dimples 30. Since the amount of medication 12 dispensed is determined unobjectively, an exact amount of medication 12 is dispensed to the child. With prior applicators, exceeding the recommended dosage of teething medication applied to the child's gums is a common event. Over-medication is often caused by misreading an applicator's dosage markings and/or from applying medication to the entire mouth when the child's pain is localized.

Since the teether 14 is intended to be inserted partially in a child's mouth by the child, the teether 14 is preferably made of lightweight, non-toxic and dishwasher safe plastic that will not easily chip, splinter, crack or otherwise tear apart. The teether 14 is preferably made of sturdy, one piece construction. Furthermore, the diameter and thickness of the chewing portion 28 are sized to partially fit in a child's mouth and deliver medication 12 to the child's gums, but is too large to be completely inserted into the child's mouth. The chewing portion 28 preferably has a diameter of about 40 to 80 mm, more preferably about 50 to 60 mm, and a thickness of 6 to 12 mm, more preferably 7 to 10 mm. In length, the teether 14 is preferably about 100 to 180 mm, more preferably about 110 to 120 mm, long. For a ring shaped handle 24, the dimensions of the handle are preferably proportional to the chewing portion 28. Accordingly, the exterior diameter of the handle 24 is preferably about 40 to 80 mm, more preferably 50 to 60 mm, and the thickness is preferably 6 to 12 mm, more preferably 7 to 10 mm. The interior diameter of the handle 24 is of cooperating dimension, preferably 28 to 46 mm, more preferably 36 to 40 mm.

The gel applicator 20 is used to fill the dimples 30 with medication 12 originating from the ampule 22. Referring now to FIGS. 1–7, the gel applicator 20 is preferably composed of plastic and includes an upper housing 40 with a flange 42, a body 44, spaced-apart forks 46, and a wiper 56.

The housing 40 defines an interior chamber 41 having a bottom wall 43 with a central opening 45 formed therein. As will be discussed more fully later, the interior chamber 41 is adapted to receive the ampule 22. The opening 45 in the interior chamber 41 permits the interior chamber 41 to communicate with a channel 48 extending through the body 44. A plurality of sharpened projections or cutters 47 are arranged around the opening 45 and extend upwardly from the bottom wall 43. The cutters 47 are adapted to burst or pierce a thin wall or membrane composed of plastic, metal foil, or other material. Preferably, the cutters 47 are semi-conical or pyramidal in shape and have pointed ends or tips.

The forks 46 are arranged parallel to one another and each have a proximal end 58 and a distal end 60. The forks 46 are joined at their proximal ends 58 to the body 44 and are outwardly displaceable so that the gel applicator 20 may be snap fit onto the teether 14, as will described more fully below. The forks 46 and the wiper 56 define a dispensing channel 50, which is in communication with the channel 48 extending through the body 44. As will be described more fully below, the dispensing channel 50 directs medication 12 to the dimples 30 in the chewing portion 28. In this manner, the forks 46 and the wiper 56 comprise a guide or guide structure for directing the medication 12 to a desired location, i.e., the dimples 30.

The distal ends 60 of the forks 46 are provided with inwardly-directed projections 66 adapted to engage indentations 68 (shown in FIGS. 2, 6, and 7) defined by the top surface 34 and bottom surface 36 of the chewing portion 28. More specifically, the projections 66 are semi-spherical. When the projections 66 are placed against the edge 38 of the chewing portion 28 and the gel applicator 20 is pushed towards the center of the chewing portion 28, the curved edge 38 of the chewing section 28 pushes the projections 66 outward, thereby flexing the forks 46 away from the top and bottom surfaces 34, 36. The projections 66 then travel along the respective top and bottom surfaces 34, 36 until the projections 66 are received into the indentations 68 and the gel applicator 20 snaps into place. To remove the gel applicator 20, the gel applicator 20 is pulled away from the teether 14 in an opposite fashion.

The projections 66 also serve to provide a pivot point for the gel applicator 20. Accordingly, the indentations 68 are preferably placed at the center of the chewing portion 28 so that the gel applicator 20 will rotate in a circular path around the chewing potion as shown by arrows 70 in FIG. 1. The gel applicator 20 will travel completely around the chewing portion 28 until the head portion 44 contacts the handle 24. In order to further limit rotational travel of the gel applicator 20 the teether 14 is provided with stop surfaces 72 formed by a raised portion 74 on the teether 14. The stop surfaces 72 engage the sides of the forks 46.

The gel applicator 20 is provided with medication from the ampule 22. Referring now to FIG. 8, there is shown a cross-sectional view of the ampule 22 mounted on a backing strip 80. The ampule 22 is generally bullet-shaped, and includes an inner sleeve 82 and an outer sleeve 84.

The inner sleeve 82 is relatively thick and is composed of a rigid material, such as hard plastic. Preferably, the inner sleeve 82 is composed of a mixture of high density polyethylene (HDPE) and low density polyethylene (LDPE). The inner sleeve 82 preferably has a hollow interior 86 and an open end 88. An annular flange 90 is disposed around the open end 88 and extends radially outward therefrom. The inner sleeve 82 further includes a closed end 92 with a concave depression 94 formed therein. As will be described more fully later, the concave depression 94 defines a nest 96 for receiving the cutters 47 of the gel applicator 20.

The outer sleeve 84 is disposed over the inner sleeve 82 and includes a convex end wall 98 spaced from the closed end 92 of the inner sleeve 82 so as to form a pocket or blister 99 therebetween. The blister 99 is filled with a precise charge of medication 12. Preferably, the charge of medication 12 is premeasured to provide the precise amount of medication 12 necessary to fill the dimples 30. The outer sleeve 84 is relatively thin and is composed of a frangible material that can be easily punctured or burst, such as metal foil, plastic, soft plastic, polyethylene, other polyolefins, polypropylene, polystyrene, polyacrylic, ABS, EVA, PVC, PET, PETG, engineering-grade plastics, or any material which may be easily drawn and is burstable. Preferably, the outer sleeve 84 is composed of LDPE.

Referring now to FIGS. 9A–9E, the manufacture of a plurality of ampules 22 will be described. As shown in FIG. 9A, a first sheet 100 of a rigid material, such as a mixture of HDPE and LDPE, is drawn, formed, stamped, punched, or otherwise deformed to form a plurality of depressions 102 having concave ends, each of said depressions 102 comprising an inner sleeve 82. In a similar manner, a second sheet 104 of a thin frangible material, such as LDPE or the other materials mentioned above, is drawn, formed, stamped, punched, or otherwise deformed as shown in FIG. 9B to form a plurality of depressions 106. The depressions 106 are deeper than the depressions 102 and have convex ends. Each of the depressions 106 comprise an outer sleeve 84.

After the outer sleeves 84 are formed, a dispensing machine 110 fills each of the outer sleeves 84 with medication 12, up to the top of the convex wall 98 and the blister 99. The first sheet 100 is then disposed over the second sheet 104, with the inner sleeves 82 and the outer sleeves 84 aligned. The first and second sheets 100, 104 are then joined together by heat sealing and/or adhesive or other means such that the inner sleeves 82 are nested in the outer sleeves 84, with the medication 12 disposed in between. The nested inner and outer sleeves 82, 84 form a plurality of the ampules 22, as shown in FIG. 9C.

Once the first and second sheets 100, 104 are joined together, the ampules 22 are die cut from the first and second sheets, as shown in FIG. 9D. Subsequently, the flanges of the ampules 22 are releasably secured to the backing strip 80, such as by heat sealing, a pressure-sensitive adhesive, or other means, as shown in FIG. 9E. The backing strip 80 is preferably a metal foil to permit the ampules 22 to be facilely peeled from the backing strip 80.

In lieu of first cutting the ampules 22 from the first and second sheets and then securing the ampules 22 to the backing strip 80, the backing strip 80 may be secured to the ampules 22 before the ampules 22 are cut from the first and second sheets. In such event, the ampules 22 are die cut from the first and second sheets 100, 104 from underneath so as to not cut the backing strip 80.

In FIGS. 9A–9E, the ampules 22 are shown being manufactured in strips of six ampules 22. Of course, the ampules 22 may be manufactured in strips having more or less ampules 22, as well as in blocks of ampules 22, or in individual ampules 22.

In order to dispense medication 12 from the ampule 22 to the dimples 30, the gel applicator 20 is attached to the chewing portion 28, as described above. An ampule 22 containing the medication 12 is peeled from the backing strip 80 and inserted into the gel applicator 20. More specifically, the ampule 22 is inserted into the interior chamber 41 of the housing 40 of the gel applicator 20, such that the end wall 98 is disposed just above the cutters 47, as shown in FIG. 6.

Once the ampule 22 is positioned as described above, the ampule 22 is pushed downwardly by applying force to the flange 90 of the inner sleeve 82 with a thumb or other digit. As a result, the end wall 98 is pressed into the cutters 47, which puncture or burst the end wall 98, thereby causing medication 12 to flow from the ruptured blister 99 into the interior chamber 41. Continuing downward movement of the ampule 22 causes the inner sleeve 82 to function as a piston or plunger that forces the medication 12 out of the interior chamber 41 and into the channel 48 through the opening 45. The concave depression 94 helps direct the medication 12 through the opening 45. From the channel 48, the medication 12 travels into the dispensing channel 50.

The gel applicator 20 is rotated around the chewing portion 28 as the ampule 22 is pushed into the interior chamber 41 of the housing 40, thereby depositing the medication 12 into the dimples 30 from the dispensing channel 50. As described above, the charge of medication 12 in the ampule 22 is preferably premeasured to provide the precise amount of medication 12 necessary to fill the dimples 30. Thus, the ampule 22 is pushed into the interior chamber 41 of the housing 40 until the closed end 92 of the inner sleeve 82 contacts the bottom wall 43, as shown in FIG. 7. With the ampule 22 in this position, the cutters 47 are disposed in the nest 96 formed by the concave depression 94. Thus, the nest 96 permits substantially the entire charge of medication 12 to be forced out of the interior chamber 41, while protecting the cutters 47 from being damaged by the closed end 92 of the inner sleeve 82.

Referring now to FIG. 4, the wiper 56 is disposed on the interior sides of the forks 46 so that the wiper 56 circumscribes the gel dispensing channel 50, except in the area where the channel 48 communicates with the gel dispensing channel 50. The wiper 56 prevents excess medication 12 from being deposited on the top surface 34, bottom surface 36, or edge 38 of the chewing portion 28 as the gel applicator 20 is rotated. It should be understood that the gel dispensing channel 50 is preferably located on both forks 46 so that medication 12 will be deposited into dimples 30 on both the top 34 and bottom 36 surfaces of the teether 14.

It should be appreciated that the use of the ampule 22 with the gel applicator 20 provides numerous benefits. Since the ampule 22 provides the precise amount of medication 12 necessary to fill the dimples 30 of the teether 14, the ampule 22 removes the guesswork in providing medication 12 to the gel applicator 20. Accordingly, providing excessive or deficient amounts of medication 12 to the teether 14 is avoided.

Since the ampule 22 holds only enough medication 12 for one application, i.e., is a "one shot" container, the medication 12 remains in a sealed environment until just before it is used, thereby helping avoid contamination or degradation of the medication 12, such as may occur if the medication 12 were stored in a conventional vile or container, which is unsealed after a first use.

Referring now to FIGS. 10 and 11 there is shown a second embodiment of the present invention. More specifically, FIGS. 10 and 11 show a gel applicator 120 adapted for use with the ampule 22. The gel applicator 120 includes a housing 122 joined at a flange 124 to a body 126 having a tapered free end 127. The body 126 is adapted for insertion into a human mouth to place the free end 127 adjacent to an affected area, such as a canker sore or around a tooth. Preferably, the body 126 is elongated and tubular.

A conduit or lumen 134 (shown in phantom) extends through the body 126 and the free end 127. As will be described more fully below, the lumen 134 conveys medication to the affected area. In this manner, the body 126 comprises a guide or guide structure for directing the medication 12 to a desired location, i.e., the affected area.

The housing 122 defines an interior chamber 128 having a bottom wall 130 with a central opening 132 formed therein. The interior chamber 128 is adapted to receive the ampule 22. The opening 132 in the interior chamber 128 permits the interior chamber 128 to communicate with the lumen 134 extending through the body 126 and the free end 127. A plurality of sharpened projections or cutters 136 are arranged around the opening 132 and extend upwardly from the bottom wall 130. The cutters 136 are adapted to burst or pierce a thin wall or membrane composed of plastic, metal foil, or other material. Preferably, the cutters 136 are semi-conical in shape and have pointed ends.

In order to dispense medication 12 from the ampule 22 to the affected area in the mouth, the ampule 22 is inserted into the interior chamber 128 of the housing 122 of the applicator 120, such that the end wall 98 is disposed just above the cutters 136. The body 126 of the applicator 120 is then inserted into the mouth and positioned to place the free end 127 adjacent to the affected area. Once the free end 127 is properly positioned, the ampule 22 is pushed downwardly by applying force to the flange 90 of the inner sleeve 82 with a thumb or other digit. As a result, the end wall 98 is pressed into the cutters 136, which puncture or burst the end wall 98, thereby causing medication 12 to flow from the ruptured blister 99 into the interior chamber 128. The medication 12 is forced out of the interior chamber 128 and into the lumen 134 through the opening 132. The medication 12 leaves the lumen 134 and coats the affected area.

Referring now to FIGS. 12–14, there is shown a third embodiment of the present invention. More specifically, FIGS. 12–14 show a teething gel system 150 adapted for use with the burstable ampule 22 containing medication 12. In contrast to the teething gel system 10 of the first embodiment, the teething gel system 150 is adapted for use by an adult. The teething gel system 150 generally includes a teether 152, and a gel spreader or gel applicator 154. The teether 152 generally has the appearance of a conventional tooth brush, and includes a handle 156, a neck 158, and a chewing portion 160 provided with depressions or dimples 162 used to hold the medication 12.

The handle 156 has a shape that is easily grasped and held by an adult. Preferably, the handle 156 has an elongated, generally rectangular shape with rounded edges. The handle 156 tapers into the neck 158, which is, in turn, joined to the chewing portion 160. The neck 158 is elongated and has a narrower cross section than the handle 156 to facilitate insertion into the mouth.

The chewing portion 160 is preferably ellipsoidal in shape and has a top surface 164, a bottom surface 166 (shown in FIG. 13) and a circumferential edge 168. The circumferential edge 168 is rounded over to form a continuously smooth surface extending from the top surface 164 to the bottom surface 166. As mentioned, the chewing portion 160 is provided with a series of dimples 162. Each dimple 162 is preferably hemispherically shaped and about 1.5 to 6 mm in diameter, more preferably 2 to 3 mm in diameter, and about 0.5 to 3 mm in depth, more preferably 1 to 1.5 mm in depth. The dimples 162 are arranged on both the top surface 164 and the bottom surface 166. The dimples 162 hold the medication 12 by surface tension.

Since the teether 152 is intended to be inserted into an adult's mouth, the teether 152 is preferably made of lightweight, non-toxic and dishwasher safe plastic that will not easily chip, splinter, crack or otherwise tear apart. The teether 152 is preferably made of sturdy, one piece construction. Furthermore, the diameter and thickness of the chewing portion 160 are sized to completely fit into an adult's mouth and deliver medication 12 to the adult's gums.

The gel applicator 154 is used to fill the dimples 162 with medication 12 originating from the ampule 22. The gel applicator 154 is preferably composed of plastic and includes an upper housing 170 with a flange 172, and a pair of spaced apart forks 174 defining a dispensing channel 175.

Referring now to FIG. 14, the housing 170 defines an interior chamber 176 having an interior wall or bottom wall 178 with a central opening 180 formed therein. Bottom wall 178 has a top surface 191 and a bottom surface 193. The interior chamber 176 is adapted to receive the ampule 22. The opening 180 in the interior chamber 176 permits the interior chamber 176 to communicate with the dispensing channel 175 formed by the forks 174. A plurality of sharpened projections or cutters 182 are arranged around the opening 180 and extend upwardly from the interior wall or bottom wall 178. The cutters 182 are adapted to burst or pierce a thin wall or membrane composed of plastic, metal foil, or other material. Preferably, the cutters 182 are semi-conical in shape and have pointed ends.

The forks 174 are arranged parallel to one another and each have a proximal end 184 and a distal end 186. The forks 174 are joined at their proximal ends 184 to the flange 172 and are resiliently movable in an outward direction. Each of the forks 174 is generally rectangular and has inwardly-curved side portions 188 conforming to the circumferential edge 168. The distal ends 186 are inwardly curved and terminate in edges 187. As set forth above, the forks 174 define a dispensing channel 175, which is in communication with the opening 180 in the bottom wall 178 of the housing 170. As will be described more fully below, the dispensing channel 175 directs medication 12 to the dimples 162 in the chewing portion 160. In this manner, the forks 174 comprise a guide or guide structure for directing the medication 12 to a desired location, i.e., the dimples 162.

When the distal ends 186 of the forks 174 are placed against a top portion of the circumferential edge 168 of the chewing portion 160 and the gel applicator 154 is pushed linearly along the length of the teether 152, toward the handle 156, the curved circumferential edge 168 of the chewing portion 160 pushes the distal ends 186 outward, thereby flexing the forks 174 outwardly and allowing the chewing portion 160 to pass between the forks 174. The edges 187 of the distal ends 186 travel along the respective top and bottom surfaces 164, 166 until the distal ends 186 slide over a bottom portion of the circumferential edge 168 at a juncture between the chewing portion 160 and the neck 158. To remove the gel applicator 154, the gel applicator 154 is pulled away from the teether 152 in an opposite fashion.

In order to dispense medication 12 from the ampule 22 to the dimples 162 in the teether 152, the gel applicator 154 is attached to the chewing portion 160, as described above. The ampule 22 is then inserted into the interior chamber 176 of the housing 170 of the gel applicator 154, such that the end wall 98 is disposed just above the cutters 182. The ampule 22 is pushed downwardly by applying force to the flange 90 of the inner sleeve 82 with a thumb or other digit. As a result, the end wall 98 is pressed into the cutters 182, which puncture or burst the end wall 98, thereby causing medication 12 to flow from the ruptured blister 99 into the interior chamber 176.

The medication 12 is forced out of the interior chamber 176 and into the dispensing channel 175 through the opening 180. From the dispensing channel 175, the medication is deposited into the dimples 162. The charge of medication 12 in the ampule 22 is preferably premeasured to provide the precise amount of medication 12 necessary to fill the dimples 162. Thus, the ampule 22 is pushed into the interior chamber 176 of the housing 170 until the closed end 92 of the inner sleeve 82 contacts the bottom wall 178.

Once the ampule 22 is pushed to the farthest extent into the interior chamber 176, the gel applicator 154 is removed from the chewing portion 160 by linearly pulling the gel applicator 154 away from the chewing portion 160 in a direction along the length of the teether 152. The edges 187 of the distal ends 186 move over the top and bottom surfaces 164, 166 of the chewing portion 160, acting like a wiper to remove excess medication 12 from the chewing portion 160. The foregoing description of the application of the medication 12 to the dimples 162 is with reference to the gel applicator 154 with the dispensing channel 175 as shown in FIG. 12 without the presence of dispensing channel or groove 190 shown in FIG. 14.

More preferably, the gel applicator 154 is provided with a dispensing channel or groove 190 as shown in FIG. 14. Channel 190 comprises a bottom wall channel or groove 198, a longitudinal channel or groove 192, and a bottom channel or groove 194. Central opening 180 communicates with bottom wall channel 198, which is a groove along the bottom surface 193 of bottom wall 178. Channel 198 then communicates with channel 192 along the inside of fork 174. Channel 192 then communicates with channel 194, the bottom wall of which forms wiper 196. As can be seen, medication 12 is forced through this channel or groove system to bottom channel 194. The forks 174 and the wiper 196 comprise a guide or guide structure for directing the medication 12 to a desired location, i.e., the dimples 162. As can be seen, this guide or guide structure is connected to the housing 170 and at least partially defines the channel 190 that is in communication with the interior chamber 176. When medication 12 is forced into this channel or groove system, channels 192 and 194 deliver medication 12 to dimples 162, with wiper 196 acting as a wiper when chewing portion 160 is withdrawn from applicator 154.

It should be appreciated that the ampule 22 may be used with medication applicators other than the teething gel system 10 of the first embodiment, the applicator 120 of the second embodiment, or the teething gel system 150 of the third embodiment.

Although particular embodiments of the invention have been described in detail, it is understood that the invention is not limited correspondingly in scope, but includes all changes and modifications coming within the spirit and terms of the claims appended hereto.

What is claimed is:

1. A burstable ampule for holding an amount of medication, said burstable ampule comprising:

an inner sleeve with a closed end, said inner sleeve being composed of a rigid material;

an outer sleeve disposed over the inner sleeve and having an end wall spaced from the closed end of the inner sleeve so as to form a pocket therebetween, said outer sleeve being composed of a frangible material, said pocket containing the medication, said inner sleeve having an open end, said outer sleeve having a closed end, said inner sleeve closed end being proximal said outer sleeve closed end, said inner sleeve open end being distal said outer sleeve closed end, said inner sleeve being more rigid than said outer sleeve.

2. The burstable ampule of claim 1, wherein the closed end of the inner sleeve has a concave depression formed therein, and wherein the end wall of the outer sleeve is convex.

3. The burstable ampule of claim 1, wherein the rigid material is polyethylene, and wherein the frangible material is polyethylene.

4. A burstable ampule according to claim 1, wherein the closed end of the inner sleeve has a concave depression formed therein.

5. A burstable ampule according to claim 1, wherein said rigid material of said inner sleeve is plastic.

6. A burstable ampule according to claim 1, wherein said rigid material of said inner sleeve is hard plastic.

7. A burstable ampule according to claim 1, wherein said inner sleeve open end is mounted on a backing strip.

8. A burstable ampule according to claim 1, wherein said ampule is generally bullet-shaped.

9. A burstable ampule according to claim 1, wherein said medication comprises an anesthetic.

10. A burstable ampule according to claim 1, wherein said outer sleeve end wall is plastic adapted to be burst by cutters.

11. A burstable ampule according to claim 1, wherein said inner sleeve is polyethylene.

12. A burstable ampule according to claim 1, wherein said inner sleeve open end has a flange extending therefrom.

13. A burstable ampule according to claim 12, wherein said flange has a backing strip attached thereto.

14. A burstable ampule according to claim 7, wherein said backing strip is metal foil.

15. A burstable ampule according to claim 4, wherein said concave depression forms a nest adapted to receive cutters.

16. A burstable ampule according to claim 1, wherein said outer sleeve end wall is metal foil adapted to be burst by cutters.

17. A burstable ampule according to claim 10, wherein said outer sleeve end wall is polyethylene.

18. A burstable ampule according to claim 7, wherein said ampule is releasably secured to said backing strip.

19. A burstable ampule according to claim 1, wherein said medication is sealed between said inner and outer sleeves.

20. A burstable ampule according to claim 1, wherein said medication is teething gel.

21. A burstable ampule according to claim 1, wherein said outer sleeve closed end is free from holes.

22. A burstable ampule according to claim 1, wherein said inner sleeve is sealed to said outer sleeve such that a top vertical portion of said inner sleeve is adapted to remain stationary with respect to an adjacent top vertical portion of said outer sleeve during discharge of said medication from said pocket.

* * * * *